United States Patent [19]

Bedford et al.

[11] Patent Number: 5,612,055

[45] Date of Patent: Mar. 18, 1997

[54] ENZYME FEED ADDITIVE AND ANIMAL FEED

[75] Inventors: Michael R. Bedford; Andrew J. Morgan, both of Marlborough, United Kingdom; Kathleen Clarkson, San Francisco, Calif.; Hagen K. Schulze, Marlborough, United Kingdom

[73] Assignees: Genecor International, Inc., Rochester, N.Y.; Finnfeeds International Limited, United Kingdom

[21] Appl. No.: 515,610

[22] Filed: Aug. 16, 1995

[30] Foreign Application Priority Data

Aug. 19, 1994 [GB] United Kingdom ............... 9416841

[51] Int. Cl.⁶ .................. A23K 1/165; A23K 1/17
[52] U.S. Cl. .................. 424/442; 435/220; 435/222; 435/223; 435/225
[58] Field of Search ................ 424/439, 442, 424/94.2, 438; 435/220, 222, 223, 225

[56] References Cited

U.S. PATENT DOCUMENTS 4,919,936  4/1990  Iwanami et al. .................. 424/442
5,441,882  8/1995  Estell et al. ...................... 435/222

*Primary Examiner*—Thurman K. Page
*Assistant Examiner*—Sharon Howard

[57] ABSTRACT

An enzyme feed additive is provided comprising a xylanase, a protease, and optionally a β-glucanase. The ratio of the units of xylanase activity per unit amount of the feed additive to the units of β-glucanase activity per same unit amount of the feed additive is 1:0–0.25.

Preferably, the xylanase is the low pI xylanase and/or the high pI xylanase obtained from *Trichoderma longibrachiatum*.

Preferably, the protease is a mutant subtilisin comprising a substitution at the amino acid residue position equivalent to tyr+217 of *Bacillus amyloliquefaciens* subtilisin with leucine.

28 Claims, No Drawings

ENZYME FEED ADDITIVE AND ANIMAL FEED

The present application is a continuation-in-part of British patent application No. 9416841.6, filed Aug. 19, 1994.

The present invention relates to an enzyme feed additive and in particular to such an additive which can decrease the feed conversion ratio of a cereal-based animal feed.

Improvements in animal feeds to enable animals to digest them more efficiently are constantly being sought. One of the main concerns is to improve the feed conversion ratio (FCR) of a feed without increasing its cost per unit weight. The FCR is the ratio of the amount of feed consumed relative to the weight gain of an animal. A low FCR indicates that a given amount of feed results in a growing animal gaining proportionately more weight. This means that the animal is able to utilise the feed more efficiently. One way in which the FCR of a feed can be improved is to increase its digestibility.

There are various constraints on the digestibility of the nutritional components of a feed such as its starch, fat, protein and amino acid contents. These constraints include:

(i) the viscosity of materials present in the animal's gut. Such viscosity is due, at least in part, to soluble non-starch polysaccharides such as mixed-linked β-glucans and arabinoxylans;

(ii) entrapment of nutrients within the cell walls of the feed, particularly those of the aleurone layer in cereals. Such entrapment is caused by the high levels of non-starch polysaccharides in the cell walls of cereals which are relatively resistant to break-down by the animal's digestive system. This prevents the nutrients entrapped within the cells from being nutritionally available to the animal; and (iii) a deficiency in endogenous enzyme activity, both of the animal and of the gut microbial population particularly in a young animal.

The above problems which interfere with digestibility are particularly noticeable in the case of cereal-based diets, such as those having a high wheat content.

Due to the problem of poor digestibility of nutrients from the feed, it is normally necessary to formulate feeds to contain significant amounts of energy providing materials in order to meet the nutritional demands of animals. Such energy providing materials conventionally include starch, fat, sugars, fibre etc. The requirement of including these energy providing materials, or sources of such materials, in a feed adds a considerable extra cost which is disadvantageous from an economic view point.

In an attempt to solve the problem of poor digestibility of cereal-based feeds, it is known to include enzyme supplements such as β-glucanases or xylanases in animal feeds. For example, WO 91/04673 discloses a feed additive for alleviating malabsorption syndrome in poultry which causes reduced digestion. The additive includes a cellulase and a xylanase. JP-A-60-75238 discloses a feed for domestic animals which contains an enzyme cocktail including protease-, cellulase-, amylase- and lipase-activities. This reference speculates that these various enzyme activities enable fermentation microbes to grow and these become useful nutritional components of the feed.

Cellulases (i.e. the cellulase system) are enzyme compositions which hydrolyze cellulose (β-1,4-D-glucan linkages) and/or derivatives thereof (e.g. phosphoric acid swollen cellulose) and give as primary products glucose, cellobiose, cellooligosaccharides, and the like. A cellulase system produced by a given microorganism is comprised of several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG") (Schulein, M., 1988). Moreover, these classifications can be further separated into individual components. For example multiple CBH components and EG components have been isolated from a variety of bacterial and fungal sources such as the cellulase enzyme complex of *Trichoderma longibrachiatum* which consists of two exo-cellobiohydrolases, CBHI and CBHII, at least three endoglucanases, EGI, EGII and EGIII, and at least one β-glucosidase. The endoglucanases and exocellobiohydrolases are considered to act synergistically in the hydrolysis of cellulose to small cello-oligosaccharides (mainly cellobiose), which are subsequently hydrolysed to glucose by the action of β-glucosidase. In addition to hydrolyzing the β-1,4 linkages in cellulose, endo-1,4-β-glucanase (EC 3.2.1.4) will also hydrolyze 1,4 linkages in β-glucans also containing 1,3-linkages. The endoglucanases act on internal linkages to produce cellobiose, glucose and cello-oligosaccharides. The exo-cellobiohydrolases act on non-reducing ends of cellulose polymers to produce cellobiose as the principal product.

Organisms which produce or express cellulase enzyme complexes often also express xylanase activity. For example, two different xylanase enzymes have been identified which are produced by *T. longibrachiatum*. The purification of these two different xylanases, one referred to as high pI xylanase (having a pI of about 9.0) and the other referred to as low pI xylanase (having a pI of about 5.2), as well as the cloning and sequencing of the gene for each xylanase is described in detail in WO 92/06209. FIG. 16 of this document sets out the deduced amino acid sequences for both the low pI and high pI gene products. Example 22 also teaches how to create *T. longibrachiatum* strains which over-express the low pI and high pI xylanase genes and which are unable to produce some or all of the non-xylanase cellulase components normally associated with *T. longibrachiatum* such as CBHI, CBHII, EGI, EGII, EGIII and BG.

As mentioned above, the use of cellulases and xylanases in animal feeds is known as is the use of proteases. It is found however that many naturally occurring sources of xylanase contain a significantly greater relative activity of β-glucanase. For example in natural strains of *T. longibrachiatum*, the ratio of xylanase activity to β-glucanase activity is of the order 1:5. Most surprisingly, it has been found that when a xylanase is included in a cereal-based diet at or around its optimum dosage level, the co-presence of enzymes possessing β-glucanase activity increases the FCR of the feed which is of course disadvantageous. In view of this surprising finding, it is concluded that enzymes having β-glucanase activity are not only unnecessary in feeds supplemented with a xylanase, but their presence is in fact detrimental to the benefits obtained from the presence of the xylanase and/or protease.

In the description and claims which follow, reference is made to units of xylanase activity, units of protease activity, and units of β-glucanase activity. These three activities as used in the present specification are measured by the following three assay methods.

Assay Method for Xylanase Activity

One unit of xylanase activity is the amount of enzyme which liberates one μmol of reducing sugars (expressed as xylose equivalents) from the substrate in one minute under the conditions described.

Reagents 1. 1% (w/v) xylan substrate

Add 10 ml of 0.5M sodium hydroxide to 1.0 g of xylan (Fluka 95590). Mix for 30 minutes with a magnetic stirrer. Add about 40 ml of 0.05M sodium acetate buffer, pH 5.3. Adjust pH to 5.3 with 1M acetic acid. Fill to 100 ml with 0.05M sodium acetate buffer, pH 5.3. Substrate should be mixed all the time when used.

2. 1M acetic acid

Pipette 5.7 ml of glacial acetic acid into a volumetric flask and fill to 100 ml with distilled water.

3. 0.05M sodium acetate buffer, pH 5.3

A. Dissolve 4.1 g of sodium acetate in distilled water and fill to 1000 ml with distilled water.

B. Dissolve 3.0 g of glacial acetic acid in distilled water and fill to 1000 ml with distilled water.

Adjust the pH of solution A to pH 5.3 with solution B.

4. Dinitrosalicylic acid (DNS) reagent

Suspend 20.0 g of 3,5-dinitrosalicylic acid in about 800 ml of distilled water. Add gradually 300 ml of sodium hydroxide solution (32.0 g NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until the solution is clear.

Fill to 2000 ml with distilled water and filter through a coarse sintered glass filter.

Store in a dark bottle at room temperature. The Reagent is stable for a maximum of 6 months.

Procedure

1. Enzyme sample 1 ml of enzyme dilution (in 0.05M sodium acetate buffer, pH 5.3) is equilibrated at +50° C. Add 1 ml of xylan substrate, stir and incubate at +50° C. for exactly 30 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme blank

Incubate 1 ml of xylan substrate at +50° C. for 30 minutes Add 3 ml of DNS-solution and stir. Add 1 ml of enzyme dilution (in 0.05M sodium acetate buffer, pH 5.3) and stir. Boil the mixture for exactly 5 minutes. Cool the reaction mixture in a cold water bath to room temperature and measure the absorbance at 540 nm against distilled water.

The absorbance difference between the enzyme sample and enzyme blank should be 0.3–0.5.

3. Standard curve

Prepare standard solutions from anhydrous xylose in 0.05M sodium acetate buffer, pH 5.3. Xylose concentration in the standards should be 0.05–0.5 mg/ml. Pipette 1 ml of standard solution, 1 ml of xylan substrate and 3 ml of DNS-reagent into a test tube. Stir and boil for exactly 5 minutes. Cool in a cold water bath to room temperature and measure the absorbance at 540 nm against standard blank. In the standard blank, xylose solution is replaced by 1 ml of 0.05M sodium acetate buffer, pH 5.3. Otherwise standard blank is treated like xylose standard.

Plot xylose concentration as a function of absorbance. New standard curve is prepared for every new DNS-reagent.

Calculation

The xylanase activity of the sample is calculated according to the following equation:

$$\text{Activity } (U/g) = \frac{([A(X) - A(O)] \times k + C_o) \times 1000 \times Df}{MW_{xyl} \times t}$$

wherein:

$A(X)$=absorbance of the enzyme sample $A(O)$=absorbance of the enzyme blank $k$=the slope of the standard curve $C_o$=the intercept of xylose standard curve 1000=factor, mmol →μmol $Df$=dilution factor (ml/g)

$MW_{xyl}$=molecular weight of xylose (150.13 mg/mmol)

$t$=reaction time (30 minutes)

Assay Method for Protease Activity

One unit of protease activity is the amount of enzyme which liberates from the substrate one microgram of phenolic compound (expressed as tyrosine equivalents) in one minute under the conditions described.

Reagents 1. 0.6% (w/v) casein substrate

Weigh 0.6 g of dry Hammarsten Casein (Merck 2242) into a 200 ml beaker. Moisten with a small amount (about 5 ml) of distilled water. When casein is thoroughly moistened add 20 ml of 0.2M disodium hydrogen phosphate solution. Warm the mixture at +60° C. with stirring until casein dissolves and an opal solution is obtained. Add 60 ml of distilled water and if needed 1–2 drops of octyl alcohol (anti-foam agent; similar products can be used). After cooling to room temperature, adjust the pH to 7.5 with 0.5M sodium hydroxide and 1M lactic acid. Transfer solution into a volumeric flask and fill to 100 ml with distilled water.

Substrate solution is usable for one week if stored in a cold room.

2. 0.2M $Na_2HPO_4$ solution

Dissolve 17.80 g of disodium hydrogen phosphate dihydrate in distilled water and fill to 500 ml with distilled water.

3. 0.02M NaCl solution

Dissolve 1.168 g of sodium chloride in distilled water and fill to 1000 ml with distilled water.

4. Precipitation reagent (TCA)

Dissolve 18.80 g of trichloroacetic acid ($CCl_3COOH$), 18.10 g of anhydrous sodium acetate ($CH_3COONa$) and 18.80 g of acetic acid ($CH_3COOH$) in distilled water and fill to 1000 ml with distilled water.

5. Phenol reagent

Mix one (1) part of Folin-Ciocalteau phenol reagent with one (1) part of distilled water just prior to the assay.

6. 0.55M $Na_2CO_3$ solution

Dissolve 58.295 g of disodium carbonate in distilled water and fill to 1000 ml with distilled water.

Procedure

1. Enzyme sample

Equilibrate 1 ml of enzyme dilution (in 0.02M NaCl solution) at +40° C. (for about 5 minutes). Add 5 ml of equilibrated casein substrate, stir and incubate at +40° C. for exactly 30 minutes. Add 5 ml of precipitation reagent and stir. Incubate at +40° C. for exactly 30 minutes and filter immediately with filter paper (Whatman 1 or Macherey Nagel 640 we).

Pipette 2 ml of filtrate, 5 ml of 0.55M $Na_2CO_3$ solution and 1 ml of phenol reagent. Stir and incubate at +40°

C. for 30 minutes. Cool to room temperature and measure the absorbance at 660 nm against distilled water.

2. Enzyme blank

Equilibrate 1 ml of enzyme dilution (in 0.02M NaCl solution) at +40° C. (for about 5 minutes). Add 5 ml of precipitation reagent, stir and incubate at +40° C. for exactly 30 minutes. Add 5 ml of casein substrate, stir an4 incubate at +40° C. for exactly 30 minutes. Filter immediately with filter paper (Whatman 1 or Macherey Nagel 640 we).

Treat the filtrate as the enzyme sample. The absorbance difference between the enzyme sample and the enzyme blank should be 0.2–0.5.

3. Standard curve

Prepare a tyrosine stock solution by weighing 10 mg of L-tyrosine into a volumetric flask, dissolve in 0.02M NaCl solution and fill to 100 ml with 0.02M NaCl solution.

Prepare dilutions from tyrosine stock solution in 0.02M NaCl solution as follows:

| | |
|---|---|
| 1:50 = | 2 µg/ml |
| 1:20 = | 5 µg/ml |
| 1:10 = | 10 µg/ml |
| 1:5 = | 20 µg/ml |
| 1:3 = | 33 µg/ml |
| 1:2 = | 50 µg/ml |

Pipette 2 ml of each tyrosine dilution, 5 ml of 0.55M $Na_2CO_3$ solution and 1 ml of phenol reagent. Stir and incubate at +40° C. for 30 minutes. Cool to room temperature and measure the absorbance at 660 nm against distilled water.

Plot tyrosine concentration as a function of absorbance.

Calculation

The protease activity of the sample is calculated according to the following equation:

$$\text{Activity } (U/g) = \frac{|A(X) - A(O)| \times k \times F \times Df}{t}$$

wherein:

A(X)=absorbance of the enzyme sample

A(O)=absorbance of the enzyme blank k=the slope of the standard curve

F=reaction dilution factor (=11)

Df=dilution factor (ml/g)

t=reaction time (30 minutes)

Assay Method for β-Glucanase Activity

One unit of β-glucanase activity is the amount of enzyme which liberates one µmol of reducing sugars (expressed as glucose equivalents) from the substrate in one minute under the conditions described.

Reagents 1. 1.0% (w/v) β-glucan substrate Moisten 1.0 g of mixed-linked β-(1,3)(1,4)-glucan (Biocon Biochemicals Ltd.) with 10 ml of ethanol. Add about 80 ml of distilled water and warm up to boil. Continue boiling with vigorous stirring until β-glucan is dissolved and a turbid solution is obtained. Cool the turbid solution to room temperature continuously stirring and adjust the β-glucan concentration to 1.0% (w/w) by adding distilled water. Filter through a glass fibre filter paper. The substrate can be used immediately. The substrate is usable for two days if stored in a cold room.

2. 0.1M sodium acetate buffer, pH 5.0

A. Dissolve 8.2 g of anhydrous sodium acetate in distilled water and fill to 1000 ml with distilled water.

B. Dissolve 6.0 g of glacial acetic acid in distilled water and fill to 1000 ml with distilled water.

Adjust the pH of solution A to 5.0 with solution B.

3. Dinitrosalicylic acid (DNS) reagent

Suspend 20.0 g of 3,5-dinitrosalicylic acid in about 800 ml of distilled water. Add gradually 300 ml of sodium hydroxide solution (32.0 g of NaOH in 300 ml of distilled water) while stirring continuously. Warm the suspension in a water bath (the temperature may not exceed +48° C.) while stirring until the solution is clear. Add gradually 600 g of potassium sodium tartrate. Warm the solution (the temperature may not exceed +48° C.) if needed until solution is clear.

Fill to 2000 ml with distilled water and filter through a coarse sintered glass filter.

Store in a dark bottle at room temperature. The reagent is stable for a maximum of 6 months.

Procedure

1. Enzyme sample

Equilibrate 1 ml of enzyme dilution (in 0.1M sodium acetate buffer, pH 5.0) at +30° C. Add 1 ml of β-glucan substrate, stir and incubate at +30° C. for exactly 10 minutes. Add 3 ml of DNS-reagent, stir and boil the reaction mixture for exactly 5 minutes. Cool the reaction mixture in a cold water bath to room temperature and measure the absorbance at 540 nm against distilled water.

2. Enzyme blank

Incubate 1 ml of β-glucan substrate at +30° C. for 10 minutes. Add 3 ml of DNS-solution and stir. Add 1 ml of enzyme dilution (in 0.1M sodium acetate buffer, pH 5.0) and stir. Boil the mixture for exactly 5 minutes. Cool the reaction mixture in cold water bath to room temperature and measure the absorbance at 540 nm against distilled water.

The absorbance difference between the enzyme sample and the enzyme blank should be 0.3–0.5.

3. Standard curve

Prepare standard solutions from anhydrous glucose in distilled water. Glucose concentration in the standards should be 0.1–0.6 mg/ml. Pipette 1 ml of glucose standard solution, 1 ml of distilled water and 3 ml of DNS-reagent into a test tube. Stir and boil for exactly 5 minutes. Cool in a cold water bath to room temperature and measure the absorbance at 540 nm against standard blank. In the standard blank, glucose solution is replaced by 1 ml of distilled water. Otherwise standard blank is treated like glucose standard.

Plot glucose concentration as a function of absorbance. New standard curve is prepared for every new DNS-reagent.

Calculation

The β-glucanase activity of the sample is calculated according to the following equation:

$$\text{Activity } (U/g) = \frac{([A(X) - A(O)] \times k + C_o) \times 1000 \times Df}{MW_{glu} \times t}$$

wherein:

A(X)=absorbance of the enzyme sample

A(O)=absorbance of the enzyme blank k=the slope of the standard curve

Co=the intercept of glucose standard curve

1000=factor, mmol→mol

Df=dilution factor (ml/g)

$MW_{glu}$=molecular weight of glucose (180.16 mg/mmol)

t=reaction time (10 minutes)

Based upon the above considerations, it is an object of the present invention to provide an enzyme feed additive for improving the FCR and/or increasing the digestibility of a cereal-based feed.

Accordingly, the present invention provides an enzyme feed additive comprising:

(i) a xylanase;

(ii) a protease; and optionally (iii) a β-glucanase wherein the ratio of the units of xylanase activity per g of the feed additive to the units of β-glucanase activity per g of the feed additive is 1:0–0.25.

It has been found that the inclusion of the above enzyme feed additive in the diet of an animal enables the animal to digest the diet more efficiently. Thus, the addition of the additive to a feed increases the proportion of feed protein and energy which the animal can derive from the feed. This in turn improves the FCR of the feed making it more economical in use.

It is also possible to utilise this aspect of the present invention by modifying a conventional feed by reducing its energy, and/or protein, and/or amino acid content whilst simultaneously maintaining the same nutritional levels of energy, protein, and amino acids available to the animal. This means that the amounts of costly energy and protein supplements conventionally included in an animal feed can be reduced as compared to conventional feeds. Energy supplements include fat. Protein supplements include fish-meal, meat-meal, soya-bean, rapeseed or canola. This results in a significant reduction in the cost per unit weight of the animal feed without decreasing its nutritional value. Alternatively, or even additionally, the amounts of amino acid supplements can be reduced as compared to conventional feeds which can also result in significant cost savings.

The enzyme feed additive according to the present invention can be prepared in a number of ways. For instance, it can be prepared simply by mixing different enzymes having the appropriate activities to produce an enzyme mix. This enzyme mix can be either mixed directly with a feed, or more conventionally impregnated onto a cereal-based carrier material such as milled wheat, maize or soya flour. Such an impregnated carrier also constitutes an enzyme feed additive in accordance with the present invention.

As an alternative, a cereal-based carrier formed from e.g. milled wheat or maize can be impregnated either simultaneously or sequentially with enzymes having the appropriate activities. For example, a milled wheat carrier may be sprayed firstly with a xylanase, secondly with a protease, and optionally finally with a β-glucanase. The carrier material impregnated with these enzymes also constitutes an enzyme feed additive in accordance with the present invention.

The feed additive of the present invention may be mixed directly with the animal feed, or alternatively mixed with one or more other feed additives such as a vitamin feed additive, a mineral feed additive and an amino acid feed additive. The resulting feed additive including several different types of components can then be mixed in an appropriate amount with the feed.

The feed additive of the invention including the cereal-based carrier is normally mixed in amounts of 0.01–50 g per kilo of feed, more preferably 0.1–10 g/kilo and most preferably about 1 g/kilo.

An alternative way of preparing the enzyme feed additive of the present invention is to construct by recombinant DNA techniques a microorganism which produces the desired enzymes in the desired relative amounts. This can be done for instance by increasing the copy number of the gene encoding xylanase and/or by using a suitably strong promoter in front of the xylanase gene. Alternatively or additionally the microorganism strain can be deleted for certain cellulase genes especially endoglucanases.

The enzyme feed additive provided by the present invention may also include other enzymes such as one or more of an α-amylase, a glucoamylase, a pectinase, a mannanase, an α-galactosidase, a phytase and a lipase. Enzymes having the desired activities may for instance be mixed with the xylanase and protease either before impregnating these on a cereal-based carrier or alternatively such enzymes may be impregnated simultaneously or sequentially on such a cereal-based carrier. The carrier is then in turn mixed with a cereal-based feed to prepare the final feed. It is also possible to formulate the enzyme feed additive as a solution of the individual enzyme activities and then mix this solution with a feed material pre-formed as pellets or as a mash.

It is also possible to include the enzyme feed additive in the animal's diet by incorporating it into a second (and different) feed or drinking water which the animal also has access to. Accordingly, it is not essential that the enzyme mix provided by the present invention is incorporated into the cereal-based feed itself, although such incorporation forms a particularly preferred aspect of the present invention.

The enzyme mix provided by the present invention includes a xylanase as an essential component. This xylanase can be obtained from a bacterium such as Bacillus, Streptomyces, Clostridium, Thermonospora, Microtetraspora, or Ruminococcus. However, it is more preferred that the xylanase is obtained from a fungus such as Trichoderma, Aspergillus, Humicola or Neocallimastix. It is particularly preferred that the xylanase is the low pI xylanase (pi=5.2) and/or the high pI xylanase (pI=9.0) obtained from *Trichoderma longibrachiatum* obtainable by the method of Example 22 of WO 92/06209. It is particularly preferred that the xylanase is the high pI xylanase. Such a xylanase composition has a ratio of units of xylanase activity per unit amount to the units of β-glucanase activity per same unit amount of about 1:0.005. The xylanase may be a mutant xylanase having an amino acid sequence not found in nature, such a sequence corresponding to that of a naturally occurring xylanase modified by inserting, deleting or replacing one or more amino acid residues in the naturally occurring xylanase.

It is readily understood by those skilled in the art of enzyme production that enzyme compositions such as those described herein can be prepared by several different methods. For example, an enzyme composition including a xylanase and possessing only a limited amount of β-glucanase activity, can be produced by genetically engineering a host organism expressing such xylanase such that undesired genes are deleted or modified to inactivate the gene or the expression product therefrom. Additionally, the enzyme composition may be prepared by purification methods such as purifying a specifically desirable activity (xylanase) from a whole cellulase complex. Suitable methods are described in WO 92/06209. Other purification methods which are described in U.S. Pat. No. 5,328,841 include purification using polyethylene glycol and the like. Likewise, such enzyme compositions may be prepared by fermentation optimization procedures whereby the ratio of enzyme component activities can be modified by variation of the pH, temperature, carbon source, or combinations of these, during the fermentation procedure.

According to a most preferred aspect of the present invention, the xylanase is from *T. longibrachiatum* overexpressing high pI or low pI xylanase produced from a transformed host that is lacking one or more of functional endoglucanase I (EGI), functional endoglucanase II (EGII), functional cellobiohydrolase I (CBHI) and functional cellobiohydrolase II (CBHII). The preparation of such transformed hosts and the production of high and low pI xylanases is described in WO 92/06209 mentioned above.

The xylanase which results from such a host has significantly lower levels of enzymes possessing β(1,4)-glucanase activity compared to xylanases obtained from naturally occurring sources. By using such a host, an enzyme composition can be obtained including only 0.005 units of β-glucanase activity per unit amount compared to 1 unit of xylanase activity in the same unit amount. In a preferred aspect of this invention, the enzyme feed additive includes a ratio of xylanase activity to β-glucanase activity of 1:0–0.01 and more preferably 1:0–0.005.

The ratio of the units of xylanase activity per g of the feed additive to the units of protease activity per g of the feed additive is preferably 1:0.001–1,000, more preferably 1:0.01–100 and most preferably 1:0.1–10.

The enzyme mix provided by the present invention also includes a protease as an essential component. It is preferred that the protease is a subtilisin which can be derived from the genus Bacillus, such as the strains including but not limited to *Bacillus amyloliquefaciens*, *Bacillus lentus*, *Bacillus licheniformis*, *Bacillus subtilis*, or *Bacillus alcalophilus*.

Suitable proteases include but are not limited to the following commercially available proteases: Novo NEUTRASE (TM) (commercially available from Novo Nordisk); PURAFECT (TM) (commercially available from Genencor International, Inc); SAVINASE (TM) (commercially available from Novo Nordisk); MAXACAL (TM) (commercially available from Gist-Brocades); DURAZYM (TM) (commercially available from Novo Nordisk); and MAXAPEM (TM) (commercially available from Gist-Brocades).

The subtilisin may also be a mutant subtilisin having an amino acid sequence not found in nature, such a sequence corresponding to that of a naturally occurring subtilisin modified by inserting, deleting or replacing one or more amino acid residues in the naturally occurring subtilisin. Suitable mutant subtilisins are described in EP-A-0130756 (corresponding to U.S. Pat. No. Re 34,606) (including mutations at position +155, +104, +222, +166, +33, +169, +189, +217, +156, +152); EP-A-0251446; WO91/06637 etc. The most preferred subtilisin is a mutant subtilisin which comprises a substitution at the amino acid residue position equivalent to tyr+217 of the subtilisin obtainable from *Bacillus amyloliquefaciens* with leucine.

Methods of producing such mutant subtilisins are described in detail in the publications U.S. Pat. No. Re. 34,606 and EP-A-0251446.

The protease which is included in the enzyme mix of the present invention should be free or relatively free of β-glucanase activity. This is to ensure that the resulting enzyme feed additive prepared by mixing the protease with the xylanase as previously described has the low or nil level of desired β-glucanase activity. This is less of a problem than with the xylanase component of the feed additive because microorganisms which naturally produce proteases do not necessarily produce high levels of β-glucanases.

It is found that the combination of the xylanase and the protease provided as the enzyme feed additive of the present invention have complementary and synergistic efficacies in terms of their ability to augment each other's effects to provide the advantages obtainable by the present invention of reducing the FCR of cereal-based animal feeds.

As mentioned above, the enzyme mix provided by the present invention is preferably for use as a feed additive in the preparation of a cereal-based feed.

According to a further aspect of the invention, this cereal-based feed comprises at least 25% by weight, more preferably at least 35% by weight, of wheat or maize or a combination of both of these cereals. The feed further comprises a xylanase in such an amount that the feed includes 100–100,000 units of xylanase activity per kg.; a protease in such an amount that the feed includes 100–100,000 units of protease activity per kg.; and optionally a β-glucanase. The ratio of the units of xylanase activity per kg. of the feed to the units of β-glucanase activity per kg. of the feed falls within the range 1:0–0.25.

Preferably, the amount of feed additive added to the feed is such that the resulting feed comprises respectively 1,000–10,000 units of both xylanase activity and protease activity per kg.

In a further aspect of the invention, a cereal-based feed is provided which comprises at least 25% by weight of wheat and/or maize and 100–100,000 units per kg. of a mutant subtilisin comprising a substitution at the amino acid residue position equivalent to tyr+217 of the subtilisin obtainable from *Bacillus amyloliquefaciens* with leucine.

Cereal-based feeds according to the present invention are suitable for animals such as turkeys, geese, ducks, pigs, sheep and cows. The feeds though are particularly suitable for poultry and pigs, and in particular broiler chickens.

The present invention in a further aspect provides the use of a composition including the low pI xylanase and/or the high pI xylanase obtainable from *Trichoderma longibrachiatum* and optionally a β-glucanase as a feed additive characterised in that the ratio of the units of xylanase activity per g of the composition to the units of β-glucanase activity per g of the composition is 1:0–0.25.

The above use of the composition as a feed additive produces a cereal-based feed having an improved FCR. According to a further aspect of the present invention, such a feed comprises (i) at least 25% by weight of wheat and/or maize; and (ii) the high pI xylanase and/or the low pI xylanase obtainable from *Trichoderma longibrachiatum* in such an amount that the feed includes 100–100,000 units of xylanase activity per kg.

The above use and cereal-based feed incorporating the high and/or low pI xylanase enables the animal to digest its feed more efficiently. Thus, the addition of such a xylanase containing feed additive to a feed increases the proportion of feed protein and energy which the animal can nutritionally derive from the feed. This in turn improves the FCR of the feed making it more economical in use. The feed additive including such a xylanase can of course be produced in the same way as the feed additives previously described.

The present invention is further explained by way of the following Examples.

EXAMPLE 1

Cobb male broiler chickens were fed with the wheat-based starter feed set out in Table 1 below up to 21 days of age.

TABLE 1

|  | Concentration (g/kg) |
|---|---|
| Ingredients |  |
| Wheat | 637.1 |
| Soybean meal | 300.0 |
| Limestone | 13.3 |
| Dicalcium Phosphate | 13.0 |
| DL-Methionine | 3.1 |
| Arginine | 1.2 |
| L-Lysine HCl | 1.3 |
| Vitamin mix | 1.0 |
| Mineral mix | 1.0 |
| Corn Oil | 35.0 |
| Salt | 4.0 |
| Calculated Composition |  |
| ME Kcal/kg | 3004.0 |
| CP % | 22.8 |
| Calcium % | 0.87 |
| Available Phosphorus | 0.40 |
| Methionine | 0.64 |
| Methionine + Cystine | 1.01 |
| Lysine | 1.29 |

The above starter diet of the chickens was supplemented by varying amounts of xylanase obtained from *Trichoderma viride* and/or a β-glucanase obtained from *Trichoderma longibrachiatum*. The *T. viride* was a strain mutated and selected for relatively high xylanase activity such that it produces 55 units of β-glucanase activity to 1,000 units of xylanase activity per unit amount. The chickens were divided into 24 separate groups with 30 birds in each group. The diets of the 24 groups were supplemented by one of the combinations of 0, 500, 1,000, 2,000, 4,000 and 8,000 units/kg of xylanase; and 0, 250, 500 and 1,000 units/kg of β-glucanase.

The feed conversion ratio for each of these trials was obtained and the values of this are set out in the following Table 2:

TABLE 2

| Xylanase (units/kg) | β-glucanase (units/kg) added |  |  |  | Average |
|---|---|---|---|---|---|
|  | 0 | 250 | 500 | 1,000 |  |
| 0 | 1.54 | 1.54 | 1.48 | 1.53 | 1.52 |
| 500 | 1.52 | 1.51 | 1.51 | 1.50 | 1.51 |
| 1000 | 1.47 | 1.49 | 1.52 | 1.54 | 1.51 |
| 2000 | 1.45 | 1.48 | 1.51 | 1.49 | 1.48 |
| 4000 | 1.50 | 1.51 | 1.46 | 1.49 | 1.49 |
| 8000 | 1.55 | 1.58 | 1.54 | 1.51 | 1.55 |

It is evident from the data set out in the above Table 2, that the presence of β-glucanase activity disadvantageously increases FCR values particularly, at the optimum xylanase level of around 1,000–3,000 units/kg.

From the results set out in the above Table 2, it is concluded that the units of xylanase activity present in the feed should be at least four times greater than the units of β-glucanase activity in order that an improvement in the FCR value can be obtained. Preferably the units of xylanase activity should be at least 100 times greater than the units of β-glucanase activity, and more preferably at least 1,000 times greater.

EXAMPLE 2

Several groups of Ross 1 broiler chickens (mixed sex) were fed the starter and finisher diets set out in Table 3 below for days 0–21 and 22–42 of their life. Each of these groups included 90 birds.

TABLE 3

|  | Starter | Finisher |
|---|---|---|
| Ingredient (kg/t) |  |  |
| Wheat | 612.2 | 668.9 |
| Soyabean meal 48% C.P. | 318.8 | 240.9 |
| Soya oil | 32.6 | 55.4 |
| Salt | 3.03 | 3.01 |
| DL methionine | 2.01 | 0.4 |
| Limestone | 13.8 | 14.7 |
| Dicalcium phosphate | 12.5 | 11.7 |
| Vitamin/mineral supplement | 10.0 | 10.0 |
| Calculated analysis (%) |  |  |
| Crude protein | 23.0 | 20.0 |
| Calcium | 0.90 | 0.90 |
| Total phosphorus | 0.67 | 0.63 |
| Available phosphorus | 0.42 | 0.40 |
| Fat | 4.63 | 6.82 |
| Fibre | 2.58 | 2.46 |
| Lysine | 1.21 | 0.99 |
| Methionine | 0.54 | 0.33 |
| Sodium | 0.15 | 0.15 |
| Potassium | 0.92 | 0.78 |
| Chloride | 0.24 | 0.24 |

A control group of broiler chickens did not have their diets supplemented by any enzymes. A second group Z had their diets supplemented by 3,000 units/kg of high pI xylanase produced from a transformed strain of *T. longibrachiatum* lacking functional EGI, EGII, CBHI and CBHII as described in WO 92/06209. Groups A, C, E had their diet supplemented with the same xylanase, and in addition by 2,000, 4,000 and 6,000 units/kg respectively of Novo Neutrase (TM) obtained from Novo Nordisk. Groups B, D and F had their diets supplemented with the same high pI xylanase, and in addition by 2,000, 4,000 and 6,000 units/kg respectively of a mutant subtilisin which is substituted at the amino acid residue position equivalent to tyr+217 of *Bacillus amyloliquefaciens* substilin with leucine as described in the U.S. Pat. No. Re. 34,606. The results of these tests are set out in the following Table 4.

TABLE 4

| Group | Control group | Z | A | B | C | D | E | F |
|---|---|---|---|---|---|---|---|---|
| Final Body weight, kg | 2.21 | 2.20 | 2.20 | 2.20 | 2.22 | 2.19 | 2.23 | 2.20 |
| Feed Intake, g per bird per day | 93.1 | 94.5 | 94.6 | 92.4 | 93.2 | 92.2 | 94.2 | 92.7 |

TABLE 4-continued

| Group | Control group | Z | A | B | C | D | E | F |
|---|---|---|---|---|---|---|---|---|
| FCR (mortality adjusted) | 1.85 | 1.85 | 1.85 | 1.82 | 1.85 | 1.82 | 1.82 | 1.82 |

From the above data, it can be calculated that the average FCR when using the xylanase and the protease Novo Neutrase is 1.84. On the other, the average FCR when using the xylanase and the mutant subtilisin protease of the present invention is 1.82. Each of the groups Z and A–F give rise to FCR values which are either equal to or superior to that obtained from the control group.

EXAMPLE 3

Two groups of Ross 1 male broiler chickens were each fed the wheat-based starter feed set in Table 1 of Example 1 for days 0–7. The starter feed was not supplemented with any antibiotic, anticoccidial or any enzyme.

For days 7–21, each group was fed the basic wheat-based feed set out in the following Table 5 in the form of a mash:

TABLE 5

| Ingredient | Amount (wt. %) |
|---|---|
| Soft wheat | 65.5 |
| Soybean meal 48% C.P. | 27.3 |
| Soy oil | 3.1 |
| Salt | 0.3 |
| DL methionine | 0.2 |
| Limestone | 1.4 |
| Dicalcium phosphate | 1.2 |
| Vitamin/mineral supplement | 1.0 |

A first control group of the chickens did not have their diet supplemented by any enzymes. The above wheat-based feed fed to the second test group was supplemented with enriched low pI xylanase obtained from a *Trichoderma longibrachiatum* strain lacking functional EGI, EGII, CBHI and CBHII as described in WO 92/06209. The xylanase inclusion level in the wheat diet was 184 units/kg. The control group had an average FCR of 2.00. In contrast, the test group fed the feed supplemented with low pI xylanase had an FCR of 1.89. Such a reduction in the FCR of the feed by addition of the xylanase indicates that the nutritional performance of the feed is improved.

EXAMPLE 4

Six groups each containing 12 castrated male pigs of PIC commercial genotype were respectively fed six different diets ad libitum in pellet form to assess the effect of enriched high pI xylanase obtained by *Trichoderma longibrachiatum*. At the start of the trial the pigs were all around 10 weeks of age. Thus, three basic feeds have a different maize/wheat ratio were formulated in accordance with the following Table 6 in which the amounts of the various components are expressed in terms kg/t of the feed.

TABLE 6

|  | 20% Wheat diet | 40% Wheat diet | 60% Wheat diet |
|---|---|---|---|
| Maize | 424 | 224 | 19 |
| Wheat | 200 | 400 | 600 |
| Wheat Middlings | 100 | 100 | 100 |
| Soyabean meal (44) | 200 | 200 | 200 |
| Meat and bone meal | 50 | 50 | 50 |
| Canola oil | — | — | 5 |
| L-Lysine HCl | 1.35 | 1.15 | 0.95 |
| Vitamins & Minerals | 25 | 25 | 25 |

Each diet was tested either as a control (without enzyme supplementation), or supplemented with 6,270 units of xylanase per kg of feed. The xylanase tested is an enriched high pI xylanase obtained from a *Trichoderma longibrachiatum* strain lacking functional EGI, EGII, CBHI and CBHII as described in WO 92/06209.

The results of these various tests are set in the following Table 7.

TABLE 7

| | Wheat (%) | | | | | |
|---|---|---|---|---|---|---|
| | 20 | | 40 | | 60 | |
| | Maize (%) | | | | | |
| | 42 | | 22 | | 2 | |
| | Control feed | Feed plus xylanase | Control feed | Feed plus xylanase | Control feed | Feed plus xylanase |
| Start Weight (kg) | 22.9 | 22.6 | 21.8 | 21.8 | 24.6 | 23.4 |
| Finish Weight | 75.0 | 82.7 | 78.7 | 82.2 | 78.8 | 82.8 |

TABLE 7-continued

| | Wheat (%) | | | | | |
|---|---|---|---|---|---|---|
| | 20 | | 40 | | 60 | |
| | Maize (%) | | | | | |
| | 42 | | 22 | | 2 | |
| | Control feed | Feed plus xylanase | Control feed | Feed plus xylanase | Control feed | Feed plus xylanase |
| (kg) Daily gain (g) | 930 | 1073 | 1015 | 1076 | 974 | 1061 |
| Daily feed intake (g) | 2546 | 2773 | 2680 | 2638 | 2826 | 2942 |
| FCR | 2.76 | 2.59 | 2.68 | 2.47 | 2.93 | 2.81 |

It will be seen from the results set out in Table 7 that the addition of the xylanase significantly improved daily live weight gain by an average of 9% in finisher pigs offered diets containing 60% by weight of cereals formed from different proportions of maize and wheat. Overall, both feed intake and the FCR were significantly improved.

EXAMPLE 5

Four groups of Nicholas male turkey poults were fed the maize-based starter feed described in Table 8 in the form of a mash up to 21 days of age.

TABLE 8

| Ingredient | Amount (wt. %) |
|---|---|
| Maize | 36.65 |
| Soybean meal (45.6% CP) | 55.4 |
| Animal-vegetable fat | 3.2 |
| Dicalcium phosphate | 2.3 |
| Limestone | 1.5 |
| Mineral premix | 0.3 |
| Vitamin premix | 0.3 |
| Sodium chloride | 0.15 |
| DL methionine | 0.2 |

The first control group were fed the feed of Table 8 unsupplemented. The feeds of three other test groups were supplemented respectively with 2,000 units/kg, 4,000 units/kg and 6,000 units/kg of a mutant subtilisin substituted at the amino residue position equivalent to tyr+217 of the *Bacillus amyloliquefaciens* subtilisin with leucine as described in U.S. Pat. No. Re. 34,606. The results of these tests are set out in the following Table 9.

TABLE 9

| Dietary Treatment | 21-day Body Weight (grams/poult) | FCR |
|---|---|---|
| Control Feed | 570 | 1.39 |
| Feed + 2000 U/kg of protease | 543 | 1.37 |
| Feed + 4000 U/kg of protease | 570 | 1.36 |
| Feed + 6000 U/kg of protease | 566 | 1.35 |

From the above data, it can be seen that increasing contents of the protease when added to the feed has the beneficial result of reducing the FCR of the feed.

The effect demonstrated above of improving FCR values can be obtained when feeds prepared in accordance with the present invention are fed to animals such as geese, ducks, sheep and cows, as well as to chickens, turkeys and pigs.

We claim:

1. An enzyme feed additive comprising:
   (i) a xylanase;
   (ii) a protease; and optionally
   (iii) a β-glucanase
wherein the ratio of the units of xylanase activity per g of the feed additive to the units of the β-glucanase activity per g of the feed additive is 1:0–0.25.

2. An enzyme feed additive according to claim 1, wherein the xylanase is obtained from a bacterium.

3. An enzyme feed additive according to claim 2, wherein the bacterium is Bacillus, Streptomyces, Clostridium or Ruminococcus.

4. An enzyme feed additive according to claim 1, wherein the xylanase is obtained from a fungus.

5. An enzyme feed additive according to claim 4, wherein the fungus is Trichoderma, Aspergillus, Humicola or Neocallimastix.

6. An enzyme feed additive according to claim 5, wherein the xylanase is the low pI xylanase and/or the high pI xylanase obtainable from *Trichoderma longibrachiatum*.

7. An enzyme feed additive according to claim 6, which comprises the high pI xylanase.

8. An enzyme feed additive according to claim 1, wherein the xylanase is a mutant xylanase having an amino acid sequence not found in nature, such a sequence corresponding to that of a naturally occurring xylanase modified by inserting, deleting or replacing one or more amino acid residues in the naturally occurring xylanase.

9. An enzyme feed additive according to claim 1, wherein the protease is a subtilisin.

10. An enzyme feed additive according to claim 9, wherein the subtilisin is derived from the genus Bacillus.

11. An enzyme feed additive according to claim 10, wherein the subtilisin is derived from *Bacillus amyloliquefaciens, Bacillus lentus, Bacillus licheniformis, Bacillus subtilis,* or *Bacillus alcalophilus*.

12. An enzyme feed additive according to claim 9, wherein the subtilisin is a mutant subtilisin having an amino acid sequence not found in nature, such a sequence corresponding to that of a naturally occurring subtilisin modified by inserting, deleting or replacing one or more amino acid residues in the naturally occurring subtilisin.

13. An enzyme feed additive according to claim 12, wherein the mutant subtilisin comprises a substitution at the amino acid residue position equivalent to asn+155, tyr+104, met+222, gly+166, ser+33, gly+169, phe+189, tyr+217, glu+156, or ala+152 of *Bacillus amyloliquefaciens* subtilisin with one of the other 19 naturally occurring amino acids.

14. An enzyme feed additive according to claim 13, wherein the mutant subtilisin comprises a substitution at the amino acid residue position equivalent to tyr+217 of *Bacillus amyloliquefaciens* subtilisin with leucine.

15. An enzyme feed additive according to claim 1, wherein the ratio of the units of xylanase activity to β-glucanase activity is 1:0–0.01.

16. An enzyme feed additive according to claim 15, wherein the ratio of the units of xylanase activity to β-glucanase activity is 1:0–0.005.

17. An enzyme feed additive according to claim 1, wherein the ratio of the units of xylanase activity per g of the feed additive to the units of protease activity per g of the feed additive is 1:0.001–1,000.

18. An enzyme feed additive according to claim 1, further comprising at least one of α-amylase, glucoamylase, pectinase, mannanase, α-galactosidase, phytase and lipase.

19. An enzyme feed additive according to claim 1, further comprising a carrier.

20. An enzyme feed additive according to claim 19, wherein the carrier is milled wheat, maize, soya or a by-product of any of these materials.

21. A method for improving the feed conversion ratio and/or increasing the digestibility of a cereal-based feed comprising adding to said cereal-based feed an enzyme feed additive comprising:

(i) a xylanase;

(ii) a protease; and optionally (iii) a β-glucanase wherein the ratio of the units of xylanase activity per g of the feed additive to the units of the β-glucanase activity per g of the feed additive is 1:0–0.25.

22. A cereal-based feed comprising (i) at least 25% by weight of wheat and/or maize; (ii) a xylanase in such an amount that the feed includes 100–100,000 units of xylanase activity per kg.; (iii) a protease in such an amount that the feed includes 100–100,000 units of protease activity per kg.; and optionally (iv) a β-glucanase; wherein the ratio of the units of xylanase activity per kg. of the feed to the units of β-glucanase activity per kg. of feed is 1:0–0.25.

23. A cereal-based feed according to claim 22, which comprises 1,000–10,000 units of xylanase activity per kg. and 1,000–10,000 units of protease activity per kg.

24. A cereal-based feed according to claim 22 or claim 23, comprising at least 35% by weight of wheat and/or maize.

25. A cereal-based feed comprising at least 25% by weight of wheat and/or maize and 100–100,000 units per kg. of a mutant subtilisin comprising a substitution at the amino acid residue position equivalent to tyr+217 of the subtilisin obtainable from *Bacillus amyloliquefaciens* with leucine.

26. A cereal-based feed comprising (i) at least 25% by weight of wheat and/or maize; and (ii) the high pl xylanase and/or the low pl xylanase obtainable from *Trichoderma longibrachiatum* in such an amount that the feed includes 100–100,000 units of xylanase activity per kg.

27. A method for preparing an animal feed for poultry or pigs comprising the cereal-based feed according to anyone of claims 22–26.

28. A method for preparing animal feed comprising a cereal-based feed and a composition including the low pl xylanase and/or the high pl xylanase obtainable from *Trichoderma longibrachiatum* and optionally a β-glucanase as a feed additive, characterized in that the ratio of the units of xylanase activity per g of the composition to the units of β-glucanase activity per g of the composition is 1:0–0.25.

* * * * *